United States Patent
Alfieri et al.

(10) Patent No.: US 11,149,748 B2
(45) Date of Patent: Oct. 19, 2021

(54) SYSTEM AND METHOD FOR VARYING PRESSURE FROM A PRESSURE GENERATOR

(71) Applicant: KONINKLIJKE PHILIPS N.V., Eindhoven (NL)

(72) Inventors: Richard Paul Alfieri, Delmont, PA (US); Frank Clementi, Somerset, PA (US)

(73) Assignee: Koninklijke Philips N.V., Eindhoven (NL)

( * ) Notice: Subject to any disclaimer, the term of this patent is extended or adjusted under 35 U.S.C. 154(b) by 137 days.

(21) Appl. No.: 16/212,788

(22) Filed: Dec. 7, 2018

(65) Prior Publication Data

US 2019/0175853 A1    Jun. 13, 2019

Related U.S. Application Data

(60) Provisional application No. 62/596,259, filed on Dec. 8, 2017.

(51) Int. Cl.
*F04D 29/62* (2006.01)
*F04D 27/02* (2006.01)
(Continued)

(52) U.S. Cl.
CPC ....... *F04D 29/622* (2013.01); *A61M 16/0066* (2013.01); *F04D 17/10* (2013.01);
(Continued)

(58) Field of Classification Search
CPC ...... A61M 16/0066; A61M 2205/0294; A61M 2205/3331; A61M 2205/3355;
(Continued)

(56) References Cited

U.S. PATENT DOCUMENTS 2,365,058 A * 12/1944 Crawford ............ F04D 29/4286
                                                    415/196
2,382,839 A *  8/1945 Erb ........................ F04D 29/167
                                                    415/197

(Continued)

FOREIGN PATENT DOCUMENTS

CN         103046969 A      4/2013
CN         204805102 U     11/2015
(Continued)

*Primary Examiner* — Charles G Freay
*Assistant Examiner* — Joseph S. Herrmann
(74) *Attorney, Agent, or Firm* — Daniel H. Brean (57) ABSTRACT

The present disclosure describes a system and method for varying pressure from a pressure generator without pressure generator motor speed variations. The system comprises a pressure generator housing, a centrifugal compressor housed within the housing, and at least one impeller blade. The centrifugal compressor is configured to generate a pressurized flow of gas. The pressure generator system includes a pressure adjustment body (e.g., a plate) that is movably attached to and/or within the housing, and an actuator configured to displace the pressure adjustment body with respect to the housing, such that displacement of the pressure adjustment body is configured to regulate pressure of the generated gas flow by varying a gap between the impeller blade and a surface of the pressure adjustment body.

14 Claims, 10 Drawing Sheets

(51) Int. Cl.
*F04D 29/16* (2006.01)
*A61M 16/00* (2006.01)
*F04D 17/10* (2006.01)
*F04D 25/06* (2006.01)

(52) U.S. Cl.
CPC ......... *F04D 25/06* (2013.01); *F04D 27/0246* (2013.01); *F04D 29/162* (2013.01); *A61M 2205/0294* (2013.01); *A61M 2205/3331* (2013.01); *A61M 2205/3355* (2013.01); *A61M 2205/42* (2013.01)

(58) Field of Classification Search
CPC ............ A61M 2205/42; F04D 15/0038; F04D 25/06; F04D 27/0246; F04D 29/162; F04D 29/622; F04D 17/10
See application file for complete search history.

(56) References Cited

U.S. PATENT DOCUMENTS

| | | | |
|---|---|---|---|
| 3,324,800 A * | 6/1967 | Schroeder | F04D 29/622 415/128 |
| 3,687,360 A | 8/1972 | Prew | |
| 4,439,200 A * | 3/1984 | Meyer | C10J 3/50 406/99 |
| 5,842,833 A * | 12/1998 | Reponen | F04D 13/12 417/202 |
| 6,182,657 B1 | 2/2001 | Bachak | |
| 6,273,671 B1 * | 8/2001 | Ress, Jr. | F01D 5/043 415/1 |
| 6,349,724 B1 | 2/2002 | Burton | |
| 6,591,612 B2 * | 7/2003 | Bolz | F04D 29/057 60/608 |
| 7,232,288 B2 * | 6/2007 | Tibban | F04D 7/045 415/169.1 |
| 7,789,049 B2 * | 9/2010 | Duley | F01P 7/167 123/41.47 |
| 7,871,241 B2 * | 1/2011 | Bourgeois | F04D 27/00 415/128 |
| 2007/0227540 A1 | 10/2007 | Ljungberg | |
| 2008/0085202 A1 | 4/2008 | Namiki | |
| 2013/0209247 A1 | 8/2013 | Herrmann | |
| 2014/0017060 A1 | 1/2014 | Duong | |
| 2014/0064923 A1 * | 3/2014 | Barnes | F04D 29/167 415/118 |
| 2014/0314544 A1 | 10/2014 | Norris | |
| 2015/0217073 A1 | 8/2015 | Higashiura | |
| 2016/0208816 A1 | 7/2016 | Sawyer | |
| 2016/0208817 A1 | 7/2016 | Sawyer | |
| 2017/0114801 A1 | 4/2017 | Duquette | |
| 2017/0165449 A1 | 6/2017 | Brambilla | |

FOREIGN PATENT DOCUMENTS

| | | |
|---|---|---|
| CN | 105840549 A | 8/2016 |
| GB | 2166800 A | 5/1986 |
| JP | 563170597 A | 7/1988 |
| JP | S63170597 A | 11/1988 |
| JP | H05256146 A | 10/1993 |
| JP | H06272698 A | 9/1994 |
| JP | H07275362 A | 10/1995 |
| JP | H10196380 A | 7/1998 |
| JP | H11257293 A | 9/1999 |
| JP | 2003269397 A | 9/2003 |
| JP | 2008031877 A | 2/2008 |

* cited by examiner

SYSTEM AND METHOD FOR VARYING PRESSURE FROM A PRESSURE GENERATOR

CROSS-REFERENCE TO RELATED APPLICATIONS

This patent application claims the priority benefit under 35 U.S.C. § 119(e) of U.S. Provisional Application No. 62/596,259, filed on Dec. 8, 2017, the contents of which are herein incorporated by reference.

BACKGROUND

1. Field

The present disclosure pertains to a system and method for varying fluid (e.g., gas or liquid) pressure from a pressure generation system without motor speed variations.

2. Description of the Related Art

Continuous positive airway pressure (CPAP) devices, auto CPAP devices, bi-level positive airway pressure support (BiPAP) devices, ventilators, and other pressure support devices are known. These devices typically require air flow pressure to be maintained at predetermined pressure levels. Regulation of air flow pressure levels in such devices is typically achieved by varying the rotational speed of a motor that drives a compressor or blower included in these devices. Regularly varying the rotational speed of the motor has many disadvantages including generating noise that is inconvenient to patients using these devices, putting higher stresses on the motors which causes wear and tear, and other disadvantages.

SUMMARY

Accordingly, one or more aspects of the present disclosure relate to a pressure generation system. The system comprises a housing and a centrifugal compressor housed within the housing. The centrifugal compressor includes at least one impeller blade. The centrifugal compressor is configured to generate a pressurized flow of gas and/or other fluids. The system comprises a pressure adjustment body (e.g., a plate and/or other pressure adjustment bodies as described herein) movably coupled to the housing. The system comprises an actuator configured to displace the pressure adjustment body with respect to the housing. A displacement of the pressure adjustment body is configured to regulate pressure of the generated gas flow by varying a gap between the impeller blade and a surface of the pressure adjustment body. In some embodiments, the actuator comprises one or more of a voice coil, a piezoelectric actuator, and/or other actuators. In some embodiments, the system further comprises a flexible coupler configured to movably couple the pressure adjustment body to the housing such that the pressure adjustment body forms a portion of the housing proximate to the impeller blade. In some embodiments, the pressure adjustment body comprises an inner portion and an outer portion. The outer portion is coupled to the housing via a first flexible coupler and the inner portion is coupled to the outer portion via a second flexible coupler. In some embodiments, the actuator comprises one or more actuators configured to displace the inner portion and the outer portion independently with respect to each other and the housing. In some embodiments, the pressure adjustment body comprises a flexible material and forms a portion of the housing proximate to the impeller blade.

Another aspect of the disclosure relates to a method for generating a pressurized flow of gas and/or other fluids with a pressure generation system. The pressure generation system comprises a housing, a centrifugal compressor, at least one impeller blade, a pressure adjustment body, an actuator, and/or other components. The method comprises housing the centrifugal compressor and the at least one impeller blade with the housing; generating, with the centrifugal compressor, the pressurized flow of gas; movably coupling the pressure adjustment body to the housing; and displacing, with the actuator, the pressure adjustment body with respect to the housing, wherein a displacement of the pressure adjustment body is configured to regulate pressure of the generated gas flow by varying a gap between the impeller blade and a surface of the pressure adjustment body. In some embodiments, the actuator comprises one or more of a voice coil, a piezoelectric actuator, and/or other actuators.

In some embodiments, the system further comprises a flexible coupler and the method further comprises movably coupling the pressure adjustment body to the housing with the flexible coupler such that the pressure adjustment body forms a portion of the housing proximate to the impeller blade. In some embodiments, the pressure adjustment body comprises an inner portion and an outer portion, and the actuator comprises one or more actuators. In such embodiments, the method further comprises coupling the outer portion to the housing via a first flexible coupler, coupling the inner portion to the outer portion via a second flexible coupler, and displacing the inner portion and the outer portion independently with respect to each other and the housing with the one or more actuators. In some embodiments, the pressure adjustment body comprises a flexible material and forms a portion of the housing proximate to the impeller blade.

Yet another aspect of the present disclosure relates to a system for generating a pressurized flow of gas and/or other fluids. The system comprises means for generating the pressurized flow of gas (and/or other fluids), the means for generating the pressurized flow of gas comprising at least one impeller blade; means for housing the means for generating the pressurized flow of gas; means for regulating pressure of the generated gas, the means for regulating pressure movably coupled to the means for housing; and means for displacing the means for regulating pressure with respect to the means for housing, wherein a displacement of the means for regulating pressure is configured to regulate pressure of the generated gas flow by varying a gap between the impeller blade and a surface of the means for regulating pressure.

In some embodiments, the means for displacing comprises one or more of a voice coil, a piezoelectric actuator, and/or other actuators. In some embodiments, the system further comprises means for movably coupling the means for regulating pressure to the means for housing such that the means for regulating pressure forms a portion of the means for housing proximate to the impeller blade. In some embodiments, the means for regulating pressure comprises an inner portion and an outer portion, and the means for displacing comprises one or more actuators. In such embodiments, the outer portion is coupled to the housing via a first flexible coupler, the inner portion is coupled to the outer portion via a second flexible coupler, and the one or more actuators are configured to displace the inner portion and the outer portion independently with respect to each other and the housing. In some embodiments, the means for regulating pressure comprises a flexible material and forms a portion of the means for housing proximate to the impeller blade.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
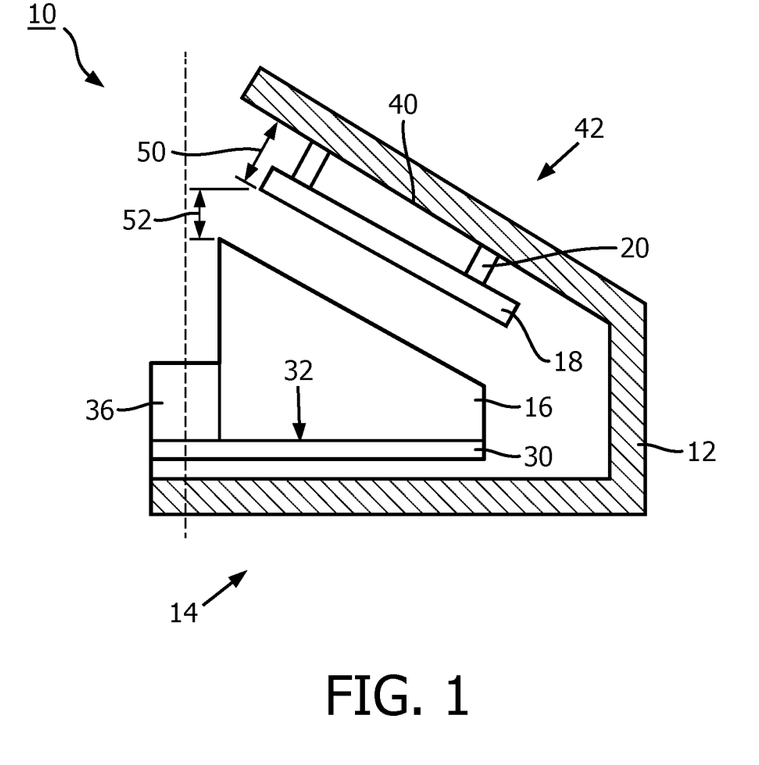
FIG. 1 illustrates a portion of an example embodiment of a pressure generation system.

FIG. 1 is a schematic illustration of a portion of an example embodiment of a pressure generation system 10. Pressure generation system 10 is configured to provide a pressurized flow of fluid (e.g., gas or liquid) for pressure support therapy and/or for other purposes. In some embodiments, pressure support therapy includes continuous positive airway pressure (CPAP) therapy, bi-level positive airway pressure support (BiPAP), ventilation, forced oscillation therapy (FOT), and/or other pressure support therapies. As described above, prior art pressure support systems typically regulate air flow pressure levels by varying the rotational speed of a motor that drives a compressor or blower included in these devices. With typical pressure support therapy systems patients often complain of the noise generated when motor speed variations occur. These variations occur to compensate for flow changes during a breath and/or for "flex" therapy. In some embodiments, "flex" therapy comprises small changes in pressure between inhalation and exhalation phases typically used in CPAP devices to improve patient comfort. Some prior art systems (such as FOT systems) cause small rapid changes in pressure. Using motor speed changes to produce the rapid pressure variation places high stresses on a typical motor and/or generates heat within the system. If prior art systems use a secondary device, such as a valve, to cause the rapid pressure changes instead of using motor speed changes, designers must find space in the systems to place the valve.

System 10 is configured to reduce or eliminate the need to change motor speeds and/or use a separate valve or other devices to maintain pressure. Instead of changing motor speeds and/or using a valve to adjust pressure, pressure generation system 10 is configured to vary a gap distance between an impeller blade 16 and the housing 12 and/or a pressure adjustment body (e.g., a plate and/or other pressure adjustment bodies) 18 of system 10. As shown in FIG. 1, pressure generation system 10 comprises one or more of housing 12, a centrifugal compressor 14, impeller blade 16, pressure adjustment body 18, an actuator 20, and/or other components. Pressure adjustment body 18 (e.g., a plate and/or other pressure adjustment bodies) is configured to move relative to impeller blade 16 (and/or portions of housing 12 as described below). By incorporating an actuated pressure adjustment body 18 (a moving surface) into housing 12, system 10 generates pressure fluctuations (e.g., for pressure support therapy such as CPAP "flex", ventilator FOT applications, and/or other therapies) and/or eliminates such fluctuations (e.g., for CPAP therapy during the course of an individual breath) based on a target therapy regime.

System 10 is configured to provide a pressurized flow of fluid (e.g., gas or liquid). In some embodiments, the pressurized flow of fluid is a pressurized flow of breathable gas for delivery to the airway of a subject. In some embodiments, system 10 is configured to deliver the pressurized flow of gas via respiratory circuit and/or other devices. System 10 receives a flow of gas from a gas source, such as the ambient atmosphere, and elevates the pressure of that gas. In some embodiments, system 10 is configured such that one or more gas parameters of the pressurized flow of gas are controlled in accordance with a therapy regime. The one or more gas parameters may include, for example, one or more of a flow rate, pressure, humidity, velocity, acceleration, and/or other parameters. The present disclosure also contemplates that gas other than ambient atmospheric air may be introduced into system 10. In some embodiments, compressor (or blower) 14 of system 10 is an unshrouded centrifugal blower. Unshrouded centrifugal blowers are compressors which do not include a cover plate for the impellers (e.g., one surface of the impeller blade is exposed). The absence of a cover allows unshrouded impellers to operate with higher rotational accelerations or tip speeds accelerations. The pressure ratio generated by an impeller is proportional to the square of the operating speed.

FIG. 1 illustrates a cross section of a portion of system 10. FIG. 1 illustrates a portion of an exemplary compressor (blower) 14 which includes a base plate 30 and a plurality of impeller blades 16. In some embodiments, the number of impellers and/or impeller blades included in a centrifugal compressor depends on how large of a compression of gas (e.g., air) and/or pressure increase is needed for a particular process (e.g., CPAP, FOT, etc.). As a result, system 10 may be configured with one or more impeller blades. In some embodiments, base plate 30 may be formed integrally with the lower side 32 of impeller blades 16. Blades 16 rotate around axis 36 to generate gas flow.

Housing 12 houses centrifugal compressor 14 and/or other components. As mentioned above, typical centrifugal compressors regulate pressure of a generated air flow by varying a speed of a motor that drives the compressor. In contrast, in some embodiments (e.g., as shown in FIG. 1), system 10 includes pressure adjustment body 18 (e.g., a plate and/or other pressure adjustment bodies) that is movably coupled to an inner surface 40 of a top portion 42 of housing 12. In some embodiments (e.g., as shown in FIGS. 2-8 and described below), pressure adjustment body 18 is coupled to housing 12 in other areas and/or forms a portion of housing 12. In the example embodiment shown in FIG. 1, pressure adjustment body 18 is driven by one or more actuators 20 such as voice coils, piezoelectric actuators, magnetic actuators, mechanical actuators, and/or other actuators to provide linear (in this example) motion of pressure adjustment body 18 in a direction represented by arrow 50 (this example is not intended to be limiting).

Actuator(s) 20 drive pressure adjustment body 18 to cause displacement of pressure adjustment body 18 such that a gap 52 between pressure adjustment body 18 and impeller blade 16 is controlled to regulate the pressure of the generated gas flow from compressor 14. This facilitates regulation of the pressure of the generated air flow without changing a rotational speed of a motor driving impeller blade 16 (e.g., such that the rotational speed of the motor may be maintained at a predetermined value). For example, system 10 is configured to cause fluctuations in CPAP, FOT, etc. air pressure provided to a subject by causing movement of pressure adjustment body 18 toward and/or away from impeller blade 16, while keeping a motor speed of a motor driving impeller blade 16 substantially constant. System 10 is configured such that a displacement of pressure adjustment body 18 toward impeller blade(s) 16 (i.e., a reduction in gap 52 between pressure adjustment body 18 and impeller blades 16) results in an increase in pressure of the generated gas flow by compressor 14, while a displacement of pressure adjustment body 18 away from impeller blades 16 (i.e., an increase in gap 52 between pressure adjustment body 18 and impeller blades 16) results in a reduction of pressure of the generated gas flow. In at least this manner, system 10 reduces stress forces on the motor of the compressor, reduces heat generation in the system, and improves patient satisfaction by eliminating noise that is usually generated by varying the speed of the motor.

Figure 2:
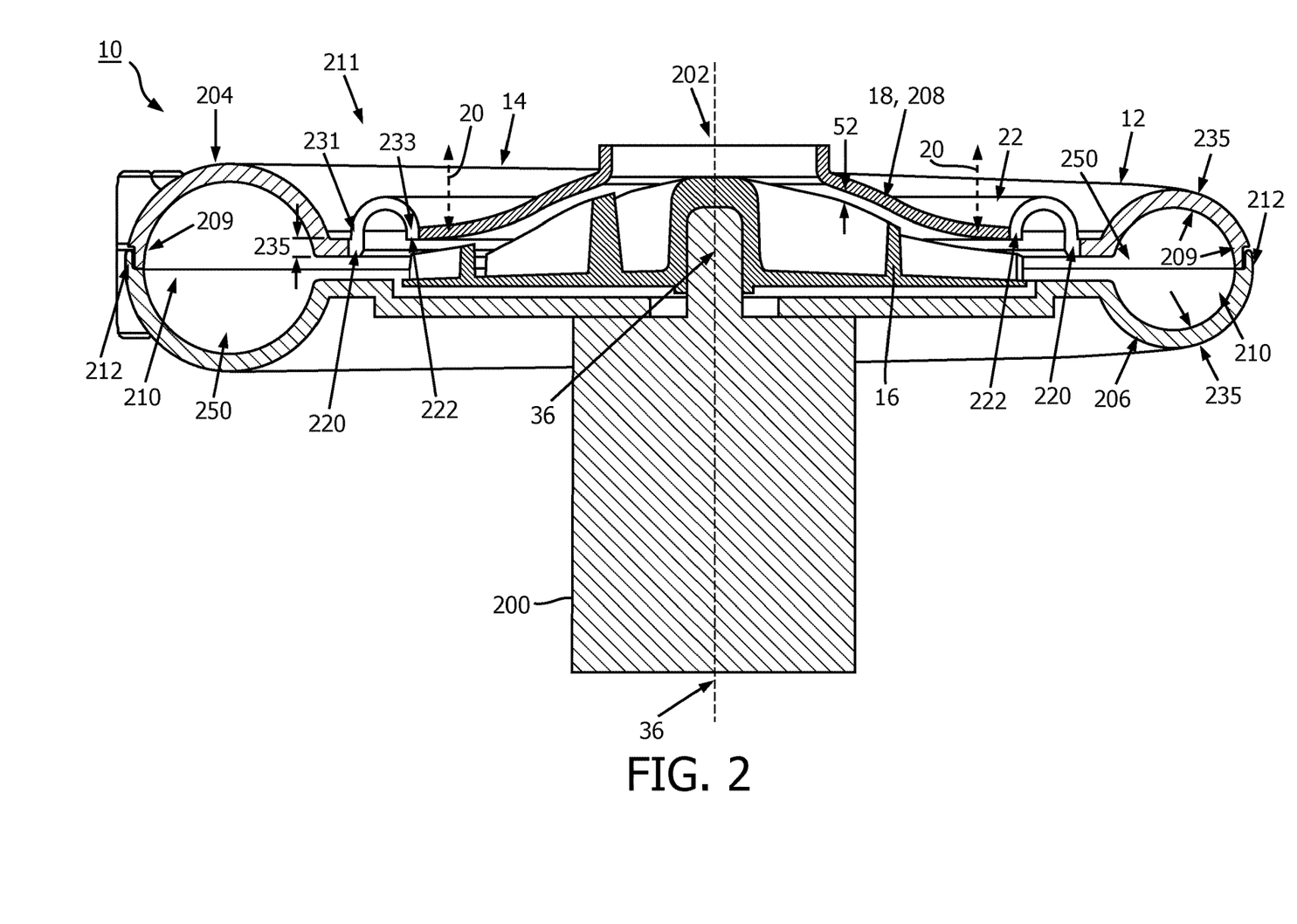
FIG. 2 illustrates another example embodiment of the system.

FIG. 2 illustrates another example embodiment of a cross section of a portion of system 10. FIG. 2 illustrates a motor 200 configured to drive impeller blade 16 of compressor 14, housing 12, pressure adjustment body 18 and other components. FIG. 2 also illustrates gap 52 which increases and/or decreases in size as a result of actuation of pressure adjustment body 18 by one or more actuators 20. As shown by cross section in FIG. 2, housing 12, pressure adjustment body 18, impeller blade 16, and/or other components of system 10 may have generally circular, disc shaped, and/or other shaped profiles. In some embodiments, at least a portion 210 of housing 12 may have a toroidal cross section and/or other cross sectional shapes. As shown in FIG. 2, housing 12 includes air inlet 202, a top fixed portion 204 of housing 12, and a bottom portion 206 of housing 12. Top fixed portion 204 and bottom portion 206 are coupled via seating features 209 and 212 formed in each portion respectively. In some embodiments, seating features 209 and 212 comprise corresponding stepped surfaces in the individual portions 204 and 206 of housing 12.

In the embodiment shown in FIG. 2, pressure adjustment body 18 forms a moveable portion 208 of housing 12. Moveable portion 208 is coupled to top fixed portion 204 via a flexible coupler 22 configured to movably couple pressure adjustment body 18 to housing 12 such that pressure adjustment body 18 forms a portion of housing 12 proximate to impeller blade 16. In some embodiments, pressure adjustment body 18 is formed in an inside 211 of toroidal portion 210 about axis 36. In some embodiment, pressure adjustment body 18 comprises one or more arcuate surfaces contoured to correspond to a shape of impeller blade 16. For example, as shown in FIG. 2, the cross section of pressure adjustment body 18 extends from flexible coupler 22 in a direction away from motor 200 along axis 36. In some embodiments, pressure adjustment body 18 forms an orifice around axis 36 that is air inlet 202.

In some embodiments, flexible coupler 22 is a flexible material positioned between pressure adjustment body 18 and housing 12 (e.g., such that it surrounds pressure adjustment body 18) configured to flex and/or bend to facilitate movement of pressure adjustment body 18 relative to other portions of housing 12 and impeller blade 16. For example, flexible coupler 22 is configured to facilitate movement of pressure adjustment body 18 toward and away from impeller blade 16. In some embodiments, flexible coupler 22 is "U" shaped and configured such that ends 220 and 222 of the "U" move toward and away from each other and/or in other directions to facilitate movement of pressure adjustment body 18 (e.g., driven by actuator(s) 20 not shown in FIG. 2). In some embodiments, a portion 231 of end 220 extends along axis 36 toward motor 200 beyond a corresponding portion 233 of end 222.

In some embodiments, portion 231 of end 220 extends along axis 36 toward motor 200 beyond corresponding portion 233 of end 222 by about a wall thickness 235 of a portion of housing 12 and/or other thicknesses. By way of non-limiting example, in some embodiments, pressure adjustment body (plate) 18 and flexible coupler 22 are and/or include an overmolded plastic part with an elastomeric and rigid material coupled to housing 12 and/or other components of the system. In some embodiments, pressure adjustment body (plate) 18 and flexible coupler 22 are coupled to housing 12 and/or other components of the system via adhesive bonds, an assembly that uses ultrasonically joined parts and/or other coupling devices and/or methods.

In the embodiment of system 10 shown in FIG. 2, pressure adjustment body 18 is configured such that an actuator (e.g., actuator 20 shown in FIG. 1 and shown by dotted line in FIG. 2) moves pressure adjustment body 18 (portion 208 of housing 12) toward and away from impeller blade 16 to vary pressure output without requiring motor speed changes for motor 200 and/or insertion of other devices such as a valve in the flow path 250 to vary pressure. System 10 is configured such that the actuator (e.g., one or more actuators 20 shown in FIG. 1) operate differently based on the application. For example, some example applications include: (1) operating at several cycles per minute to provide CFLEX therapy in CPAP. This would vary the pressure to the subject during each breath cycle. Typically this pressure variation is about +/−1 to 2 cm $H_2O$ relative to the set CPAP pressure. Some example applications include: (2) operating at several cycles per second to provide Flow Oscillation Therapy (FOT) and/or other high frequency oscillation treatment. This would vary the pressure to the patient rapidly during each inhaled breath. Typically this pressure variation is about +/−1 to 2 cm $H_2O$ relative to the IPAP pressure. Some example applications include: (3) in CPAP therapy, when the subject pressure is intended to maintain a fixed value, motor speed changes are typically required to adjust the blower pressure for varying airflow rates. With system 10, the actuator (e.g., one or more actuators 20) cause displacement of pressure adjustment body 18 to achieve pressure changes rather than motor speed variations typically used. Some example applications include: (4) using system 10 for Bi-Level therapy.

Figure 3:
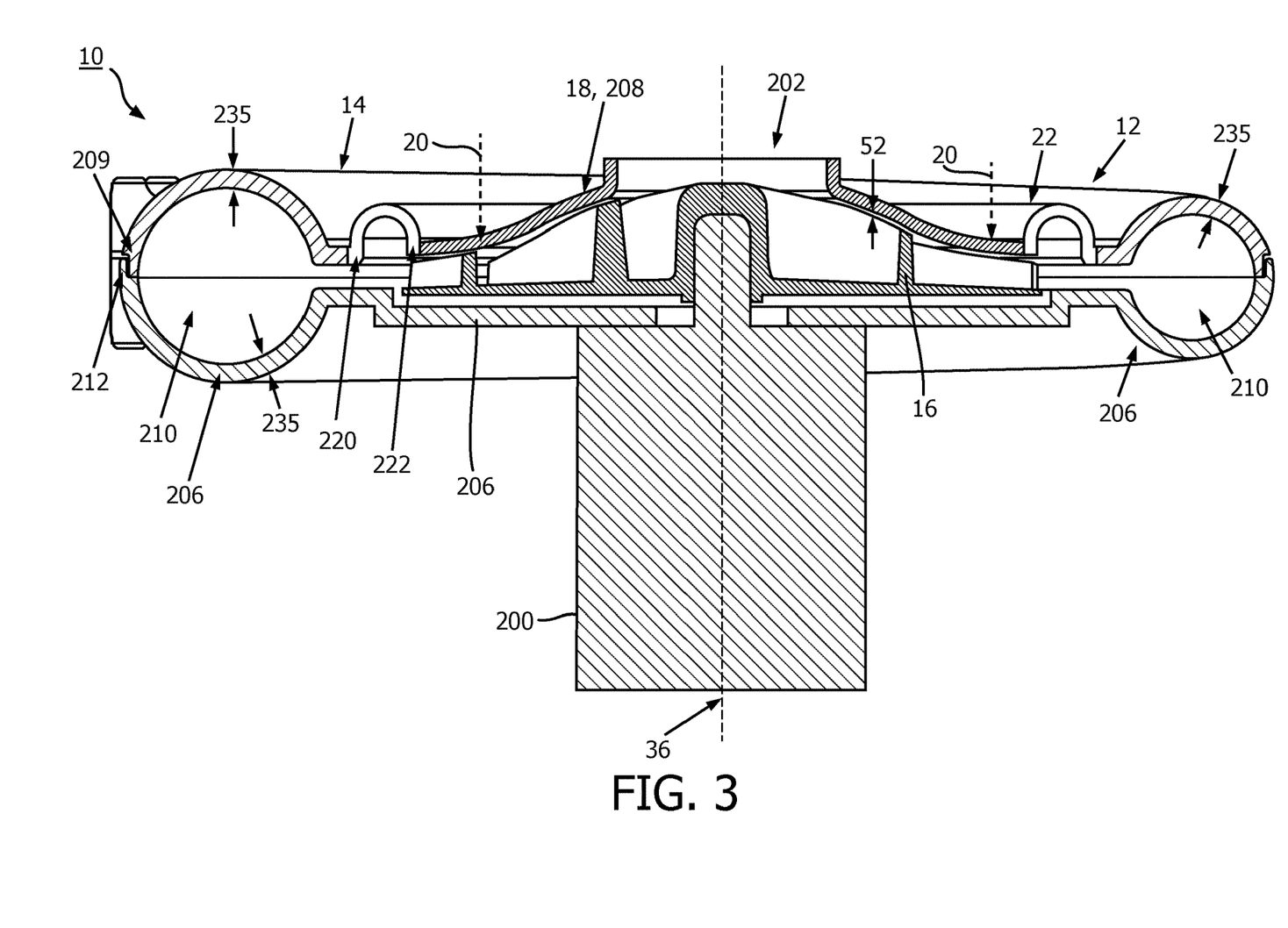
FIG. 3 illustrates an embodiment of the system showing a gap that is narrowed relative to the gap shown in FIG. 2.

FIG. 3 illustrates an embodiment of system 10 showing gap 52 narrowed relative to gap 52 shown in FIG. 2. In some embodiments, gap 52 is narrowed responsive to force applied by one or more actuators 20 that causes pressure adjustment body 18 to move toward impeller blade 16. In some embodiments, the force applied by one or more actuators 20 overcomes force applied by flexible coupler 22 which tends to keep pressure adjustment body 18 in a rest or nominal position (e.g., the position shown in FIG. 2), and also overcomes the internally generated pressure on the inside surface of pressure adjustment body 18. When gap 52 is narrowed by pressure adjustment body 18 via one or more actuators 20 and/or other components of system 10, system 10 generates increased pressure for the same motor 200 operating speed compared to the pressure generated when gap 52 is wider (e.g., as shown in FIG. 2). As shown in FIG. 3, pressure adjustment body 18 (moveable portion 208 of housing 12) is moved closer to impeller blade 16, thus generating increased pressure output for a constant operating speed relative to a nominal operating position for pressure adjustment body 18 (e.g., as shown in FIG. 2), for example.

Figure 4:
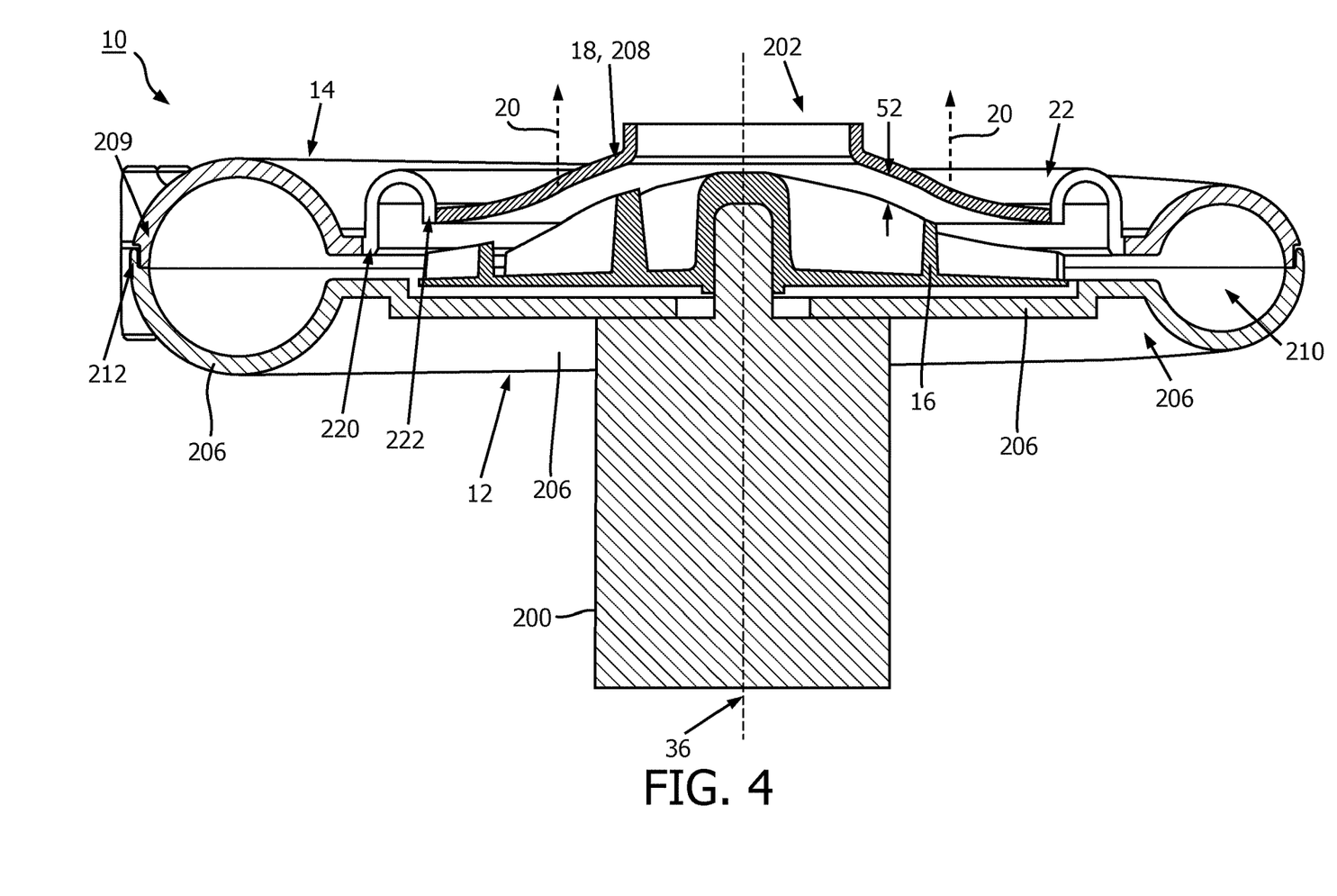
FIG. 4 illustrates an embodiment of the system showing a gap that is widened relative to the gap shown in FIG. 2.

FIG. 4 illustrates an embodiment of the system showing a gap 52 that is widened relative to the gap 52 shown in FIG. 2. In some embodiments, gap 52 is widened responsive to force applied by one or more actuators 20 that causes pressure adjustment body 18 to move away from impeller blade 16, a lack of any force applied by actuators 20, and/or other events. In some embodiments, the force applied by one or more actuators 20 overcomes force applied by flexible coupler 22 which tends to keep pressure adjustment body 18 in the rest or nominal position (e.g., the position shown in FIG. 2). When gap 52 is widened by pressure adjustment body 18 via one or more actuators 20 and/or other components of system 10, system 10 generates decreased pressure for the same motor 200 operating speed compared to the pressure generated when gap 52 is narrower (e.g., as shown in FIG. 2 and/or FIG. 3). As shown in FIG. 4, pressure adjustment body 18 (moveable portion 208 of housing 12) is moved further from impeller blade 16, thus generating decreased pressure output for a constant operating speed relative to a nominal operating position of pressure adjustment body 18, for example.

Figure 5:
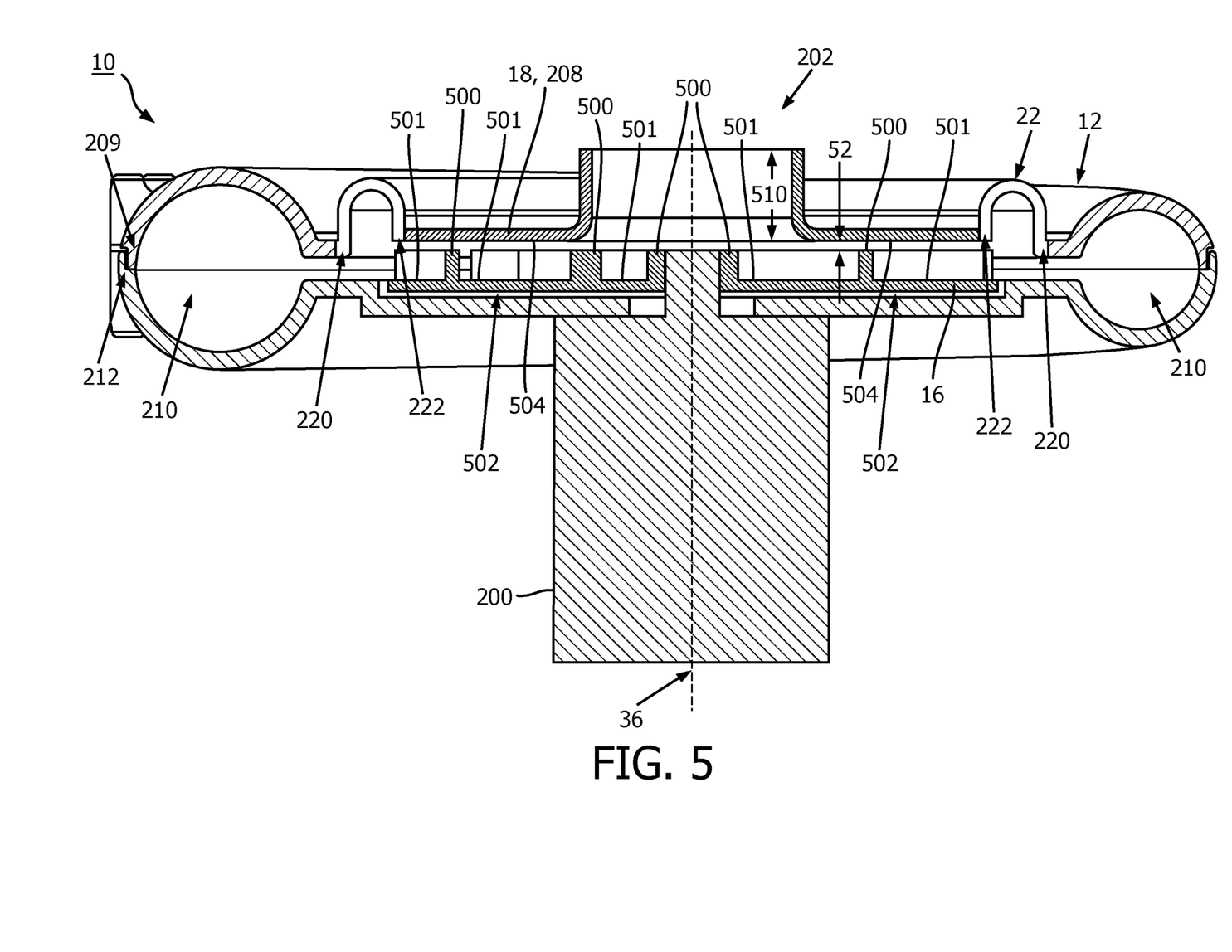
FIG. 5 illustrates another example embodiment of the system.

FIG. 5 illustrates another example embodiment of system 10. As shown in FIG. 5, in some embodiments, impeller blade 16 top 500, 501 and bottom 502 surfaces are substantially flat (e.g., within an individual surface 500 or 501) and substantially parallel. In this example, the surface 504 of pressure adjustment body 18 closest to impeller blade 16 is also substantially flat and corresponds to the surfaces 500, 501 of impeller blade 16. In this example, air inlet 202 is elongated to extend from surface 504 of pressure adjustment body 18 along axis 36 away from motor 200 (it should be noted that this is an example only and not intended to be limiting). The elongation of air inlet 202 forms an air inlet cylinder 510 (shown in cross section in FIG. 5).

Figure 6:
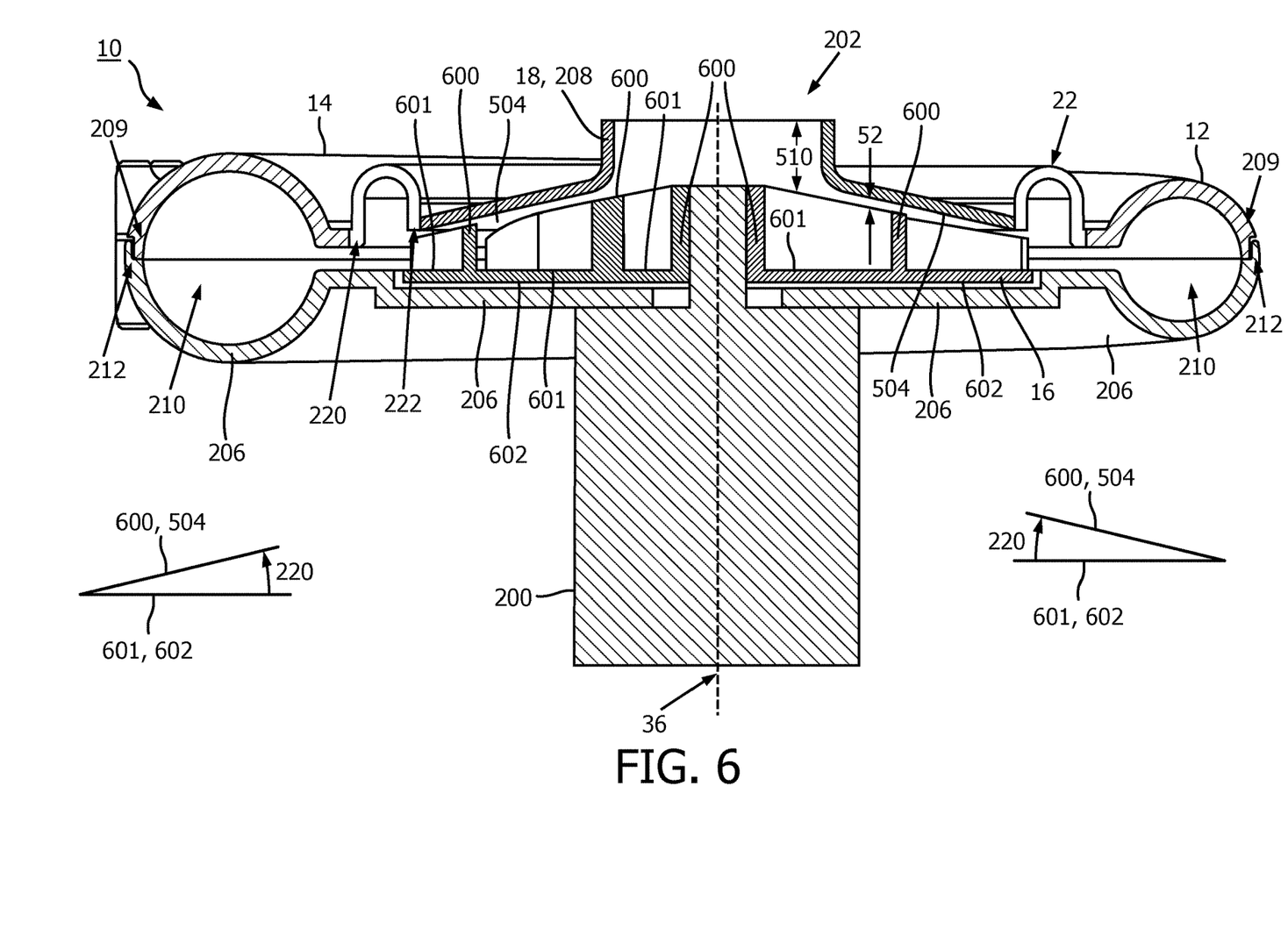
FIG. 6 illustrates another example embodiment of the system.

FIG. 6 illustrates another example embodiment of system 10. As shown in FIG. 6, in some embodiments, impeller blade 16 top 600, 601 and bottom 602 surfaces are substantially straight (e.g., within an individual surface 600 or 601), but not necessarily parallel. In this example, the surface 504 of pressure adjustment body 18 closest to impeller blade 16 corresponds to the surfaces 600 of impeller blade 16. As shown, in FIG. 6, surface 504 and surfaces 600 correspond to each other. Surface 504 of pressure adjustment body 18 and surfaces 600 of impeller blade 16 extend at an angle 220 relative to surfaces 601 and/or 602 away from surfaces 601 and/or 602 toward air inlet 202. In some embodiments, angle 220 is between about 0 and about 30 degrees.

Figure 7:
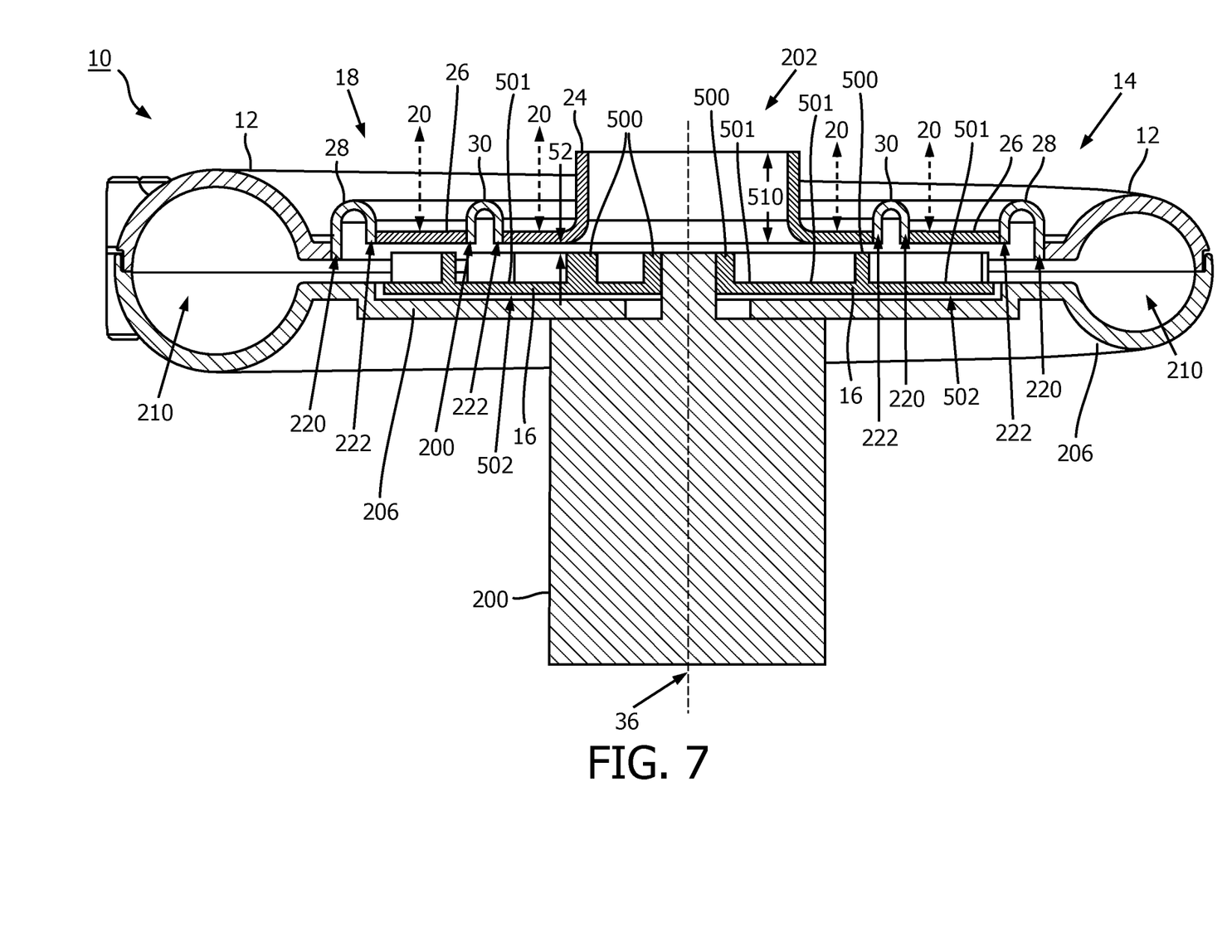
FIG. 7 illustrates another example embodiment of the system.

FIG. 7 illustrates another example embodiment of system 10. In the example shown in FIG. 7, pressure adjustment body 18 comprises an inner portion 24, an outer portion 26, and/or other portions (e.g., the two portions shown in FIG. 7 are not intended to be limiting). Outer portion 26 is coupled to housing 12 via a first flexible coupler 28, and inner portion 24 is coupled to outer portion 26 via a second flexible coupler 30. In some embodiments, housing 12, first flexible coupler 28, outer portion 26, second flexible coupler 30, and inner portion 24 form concentric rings around axis 36 and/or other shapes. In some embodiments, flexible couplers 28 and 30 are similar to and/or the same as flexible coupler 22 described above.

In some embodiments, actuator 20 comprises one or more actuators 20 configured to displace inner portion 24 and outer portion 26 independently with respect to each other and other portions of housing 12. For example, in some embodiments, gap 52 between inner portion 24 and impeller blade 16 may be different than a similar gap between outer portion 26 and impeller blade 16. In some embodiments, these gaps may be the same. Advantageously, moving a smaller portion of the surface would require less force from the actuator. It should be noted that FIG. 7 is illustrated with impeller blade 16 top 500, 501 and bottom 502 surfaces, and surfaces of pressure adjustment body 18 portions 24 and 26, substantially flat (e.g., within an individual surface 500 or 501) and substantially parallel. This is not intended to be limiting. Embodiments of system 10 having multiple pressure adjustment body 18 portions and/or multiple flexible couplers may be combined with any other embodiment (e.g., embodiments with arcuate pressure adjustment body surfaces, embodiments, with angled pressure adjustment body surfaces, etc.).

Figure 8:
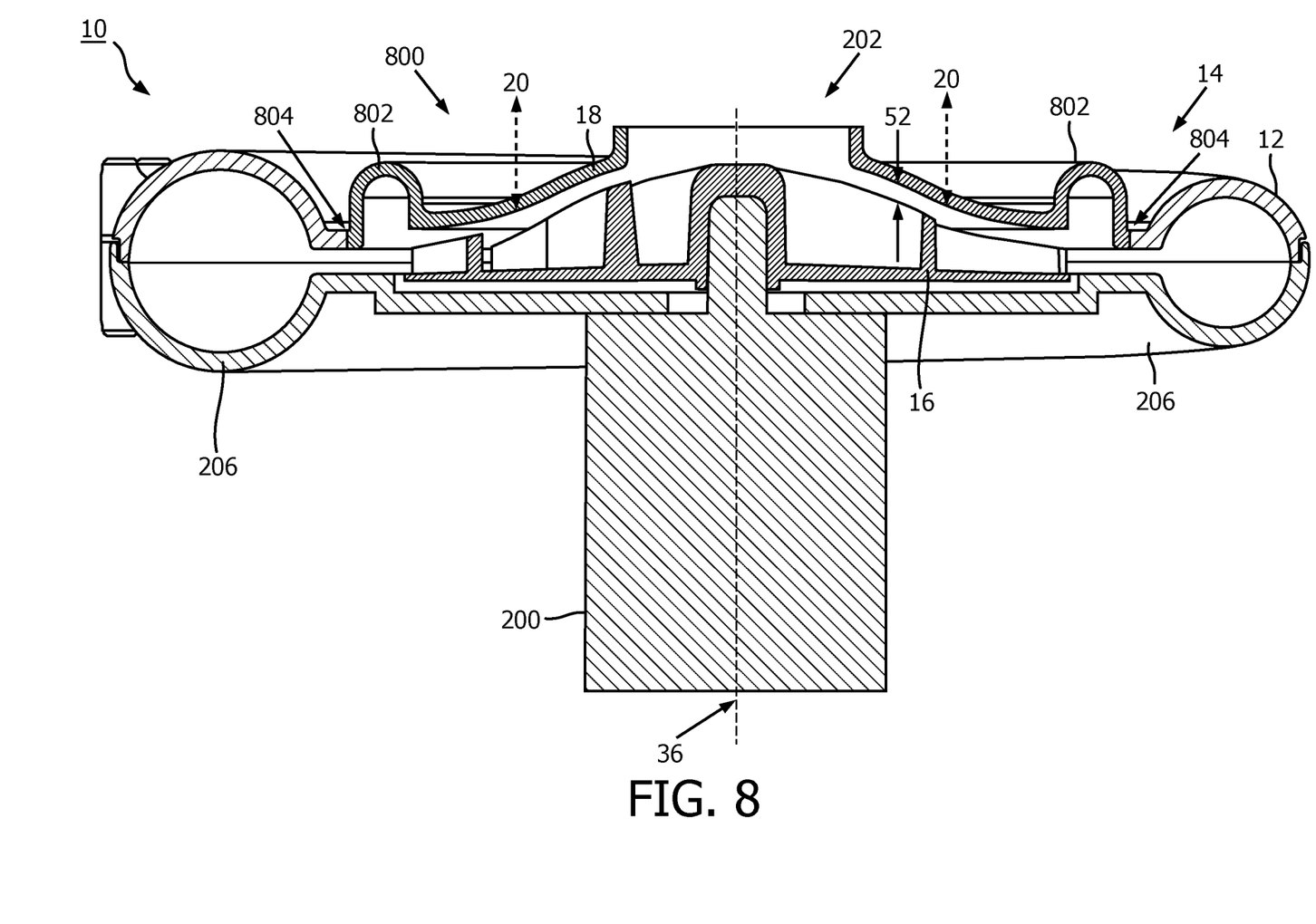
FIG. 8 illustrates another example embodiment of the system.

FIG. 8 illustrates another example embodiment of system 10. As shown in FIG. 8, pressure adjustment body 18 comprises a flexible material and forms a portion 800 of housing 12 proximate to impeller blade 16. In some embodiments, portion 800 comprises one or more materials similar to and/or the same as materials included in flexible coupler 22 described above. In some embodiments, portion 800 is configured to bend, flex, stretch, and/or otherwise change shape responsive to the application of force to one or more areas of portion 800. For example, actuator 20 may comprise one or more actuators 20 configured to displace the one or more areas of portion 800 independently with respect to each other and other portions of housing 12. In some embodiments, gap 52 between portion 800 and impeller blade 16 may vary across portion 800 depending on where actuator(s) contact portion 800 and/or based on other factors.

In some embodiments, portion 800 includes a coupling portion 802 configured to couple portion 800 to one or more additional portions of housing 12. In these embodiments, portion 800 and portion 802 are formed as a single unitary piece. In some embodiments, portion 802 may be U-shaped and/or have other shapes and be positioned at an outer edge 804 of portion 800 relative to axis 36. In some embodiments, portion 800 is coupled to housing 12 using methods similar to and/or the same as coupling methods described above used to couple flexible coupler 22, pressure adjustment body 18, housing 12, and/or other components of system 10. In some embodiments, portion 800 forms air inlet 202 at or near a center of portion 800 along axis 36. Advantageously, this embodiment may offer more control depending on the actuator method choices. Also, there is the possibility of better airflow. If the entire top surface is flexible, U-shaped feature 802 may be removed allowing better flow of the air without the disruption created by the U shape. It should be noted that in some embodiments, U shaped feature 802 may be removed all together (such that the flexibility is provided by the plate itself).

Figure 9:
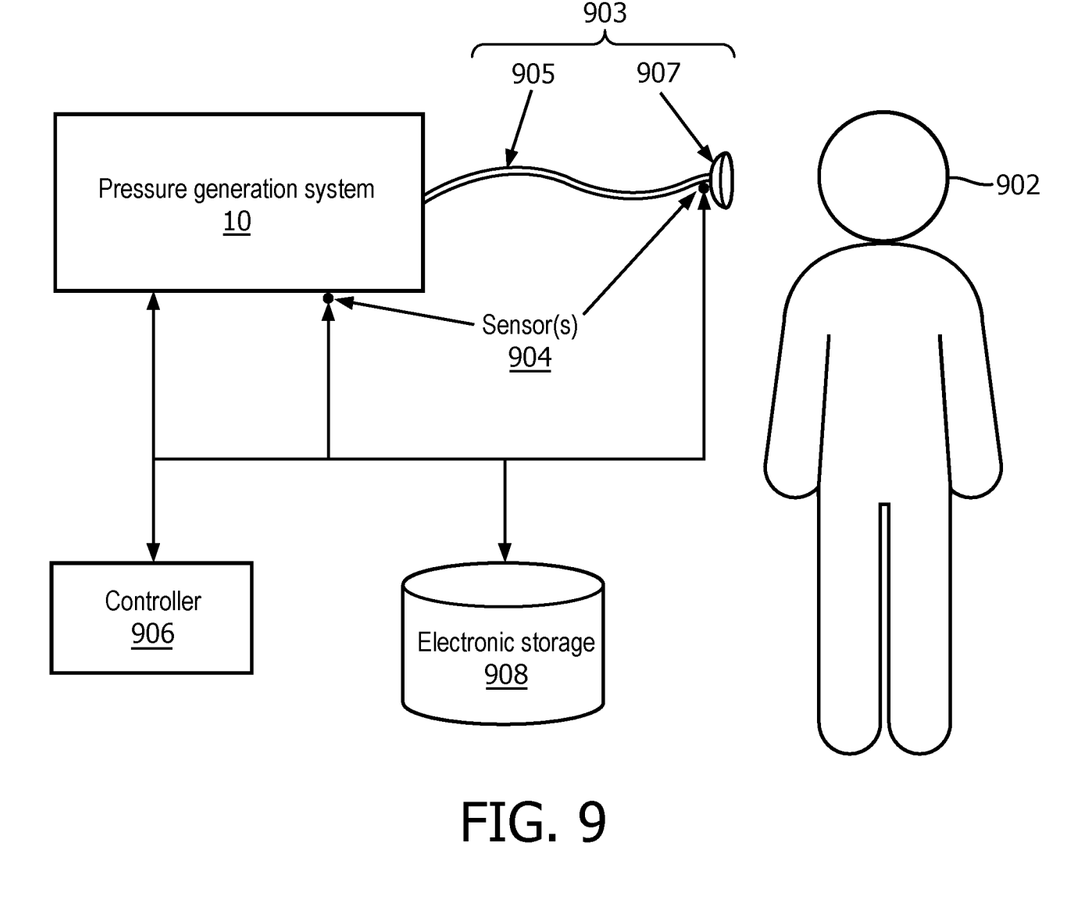
FIG. 9 illustrates the pressure generation system as a component of a pressure support system configured to provide pressure support to a subject.

FIG. 9 illustrates pressure generation system 10 as a component of a pressure support system (e.g., the whole system shown in FIG. 9) configured to provide pressure support to a subject 902. This is shown as an example only and is not intended to be limiting. As shown in FIG. 9, the pressure support system comprises pressure generation system 10, respiratory circuit 903, one or more sensors 904, a controller 906, electronic storage 908, and/or other components.

Respiratory circuit 903 is configured to deliver the pressurized flow of breathable gas from pressure generation system 10 to the airway of subject 902. Respiratory circuit 903 may be configured for any of the pressure support therapies described herein and/or other pressure support therapies. As such, respiratory circuit 903 comprises one or more conduits 905, an interface appliance 907, and/or other components. Conduit 905 may be configured to convey the pressurized flow of gas to interface appliance 907. Interface appliance 907 may be configured to deliver the flow of gas to the airway of subject 902. In some embodiments, interface appliance 907 is non-invasive. As such, interface appliance 907 non-invasively engages subject 902. Non-invasive engagement comprises removably engaging an area (or areas) surrounding one or more external orifices of the airway of subject 902 (e.g., nostrils and/or mouth) to communicate gas between the airway of subject 902 and interface appliance 907. Some examples of non-invasive interface appliances may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Sensors 904 are configured to generate output signals conveying information related to one or more gas parameters of the gas within system 10 and/or respiratory circuit 903. The one or more gas parameters comprise flow rate, volume, pressure, a composition (e.g., concentration(s) of one or more constituents), temperature, humidity, acceleration, velocity, acoustics, changes in a parameter indicative of respiration, and/or other gas parameters. Sensors 904 may comprise one or more sensors that measure such parameters directly (e.g., through fluid communication with the flow of gas in respiratory circuit 903). Sensors 904 may comprise one or more sensors that generate output signals related to one or more parameters of the flow of gas indirectly. For example, one or more of sensors 904 may generate an output based on an operating parameter of system 10 (e.g., motor current, voltage, rotational velocity, and/or other operating parameters), and/or other parameters. Although sensors 904 are illustrated at single locations within (or in communication with) respiratory circuit 903 and system 10, this is not intended to be limiting. Sensors 904 may include sensors disposed in a plurality of locations, such as for example, within system 10, within (or in communication with) interface appliance 907, and/or other locations.

Controller 906 is configured to provide information processing capabilities in the illustrated system. As such, controller 906 may comprise one or more of a digital processor, an analog processor, a digital circuit designed to process information, an analog circuit designed to process information, a state machine, and/or other mechanisms for electronically processing information. Although controller 906 is shown in FIG. 1 as a single entity, this is for illustrative purposes only. In some implementations, controller 906 may comprise a plurality of control and/or processing units. These control and/or processing units may be physically located within the same device (e.g., pressure generation system 10), or controller 906 may represent processing functionality of a plurality of devices operating in coordination.

In some embodiments, controller 906 is configured to determine one or more parameters within system 10 and/or the overall system. The one or more parameters within system 10 and/or the overall system may comprise gas parameters related to the pressurized flow of breathable gas, breathing parameters related to respiration of a subject, and/or other parameters. Controller 906 is configured to determine the one or more parameters based on the output signals of sensors 904 and/or other information. The information determined by controller 906 may be used by controller 906 to control pressure generation system 10 (e.g., motor 200, actuators 20, etc. described above) and/or for other uses.

In some embodiments, controller 906 is configured to control a position of pressure adjustment body (e.g., plate and/or other pressure adjustment bodies) 18 (FIG. 1, FIG. 2, etc.) to control pressure generated by pressure generation system 10 and/or other devices to generate the flow of gas in accordance with a ventilator regime, a positive airway pressure therapy regime, a mechanical inexsufflation regime, and/or other therapy regimes. By way of non-limiting example, controller 906 may control pressure generation system 10 such that the pressure support provided to subject 902 via the flow of gas comprises non-invasive ventilation, positive airway pressure support, continuous positive airway pressure support, bi-level support, BiPAP®, inexsufflation, and/or other types of pressure support therapy.

In some embodiments, electronic storage 908 comprises electronic storage media that electronically stores information. The electronic storage media of electronic storage 908 may comprise one or both of system storage that is provided integrally (i.e., substantially non-removable) with system 10 and/or the overall system and/or removable storage that is removably connectable to system 10 and/or the overall system via, for example, a port (e.g., a USB port, a firewire port, etc.) or a drive (e.g., a disk drive, etc.). Electronic storage 908 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 908 may store software algorithms, information determined by controller 906, information received via a user interface, and/or other information that enables system 10 and/or the overall system to function properly. Electronic storage 908 may be (in whole or in part) a separate component within the overall system, or electronic storage 908 may be provided (in whole or in part) integrally with one or more other components of the overall system (e.g., pressure generation system 10, controller 906, etc.).

Figure 10:
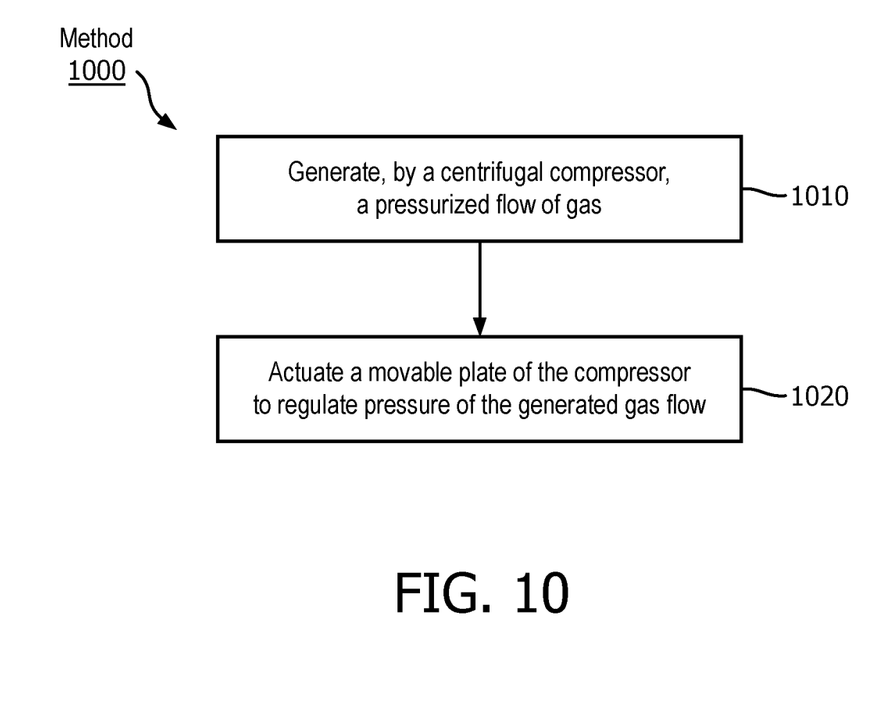
FIG. 10 depicts an exemplary flowchart illustrating a process performed by the pressure generation system.

FIG. 10 illustrates a method 1000 for generating a pressurized flow of gas with a pressure generation system. The pressure generation system comprises a housing, a centrifugal compressor, at least one impeller blade, a pressure adjustment body, an actuator, and/or other components. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1010, a pressurized flow of gas is generated by the centrifugal compressor. In some embodiments, operation 1010 is performed by a centrifugal compressor 14 and/or an impeller blade the same as or similar to centrifugal compressor 14 and/or impeller blade 16 (shown in FIGS. 2-9 and described herein).

At an operation 1020, a moveable pressure adjustment body of the compressor is actuated to regulate pressure of the generated gas flow. In some embodiments, the actuator comprises one or more of a voice coil or a piezoelectric actuator. In some embodiments, the system further comprises a flexible coupler, and operation 1020 comprises movably coupling the pressure adjustment body to a housing of the centrifugal compressor with the flexible coupler such that the pressure adjustment body forms a portion of the housing proximate to the impeller blade. In some embodiments, the pressure adjustment body comprises an inner portion and an outer portion, and the actuator comprises one or more actuators. In such embodiments, operation 1020 may comprise coupling the outer portion to the housing via a first flexible coupler, coupling the inner portion to the outer portion via a second flexible coupler, and displacing the inner portion and the outer portion independently with respect to each other and the housing with the one or more actuators. In some embodiments, the pressure adjustment body comprises a flexible material and forms a portion of the housing proximate to the impeller blade. In some embodiments, operation 1020 is performed by an actuator and a pressure adjustment body the same as or similar to actuator 20 and pressure adjustment body 18 (shown in FIGS. 2-9 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure generation system comprising:
   a housing;
   a centrifugal compressor housed within the housing and including at least one impeller blade, the centrifugal compressor configured to generate a pressurized flow of gas;
   a pressure adjustment body movably coupled to the housing, the pressure adjustment body comprising one or more arcuate surfaces contoured to correspond to a shape of the impeller blade;
   an actuator configured to displace the pressure adjustment body with respect to the housing, wherein a displacement of the pressure adjustment body is configured to regulate pressure of the generated gas flow by varying a gap between the impeller blade and the one or more arcuate surfaces of the pressure adjustment body; and
   a flexible coupler configured to movably couple the pressure adjustment body to the housing proximate to the impeller blade, the flexible coupler configured to surround the pressure adjustment body, wherein opposite ends of the flexible coupler are configured to move toward and away from each other to facilitate movement of an edge of the pressure adjustment body toward and away from the housing.

2. The system of claim 1, wherein the flexible coupler is "U" shaped and configured such that the opposite ends of the "U" move toward and away from each other to facilitate the movement of the edge of the pressure adjustment body toward and away from the housing.

3. The system of claim 1, wherein the pressure adjustment body comprises an inner portion and an outer portion, the outer portion coupled to the housing via a first flexible coupler of the flexible coupler, the inner portion coupled to the outer portion via a second flexible coupler, and wherein the actuator comprises one or more actuators configured to displace the inner portion and the outer portion independently with respect to each other and the housing.

4. The system of claim 1, wherein the centrifugal compressor is configured to receive a flow of gas from a gas source, elevate a pressure of the gas to form the pressurized flow of gas, and control one or more gas parameters of the pressurized flow of gas in accordance with a therapy regime for delivery to a subject.

5. The system of claim 1, wherein at least a portion of the housing has a toroidal cross section.

6. A method for generating a pressurized flow of gas with a pressure generation system, the pressure generation system comprising a housing, a centrifugal compressor, at least one impeller blade, a pressure adjustment body, an actuator, and a flexible coupler, the method comprising:
housing the centrifugal compressor and the at least one impeller blade with the housing;
generating, with the centrifugal compressor, the pressurized flow of gas;
movably coupling the pressure adjustment body to the housing, the pressure adjustment body comprising one or more arcuate surfaces contoured to correspond to a shape of the impeller blade;
displacing, with the actuator, the pressure adjustment body with respect to the housing, wherein a displacement of the pressure adjustment body is configured to regulate pressure of the generated gas flow by varying a gap between the impeller blade and the one or more arcuate surfaces of the pressure adjustment body; and
movably coupling the pressure adjustment body to the housing with the flexible coupler proximate to the impeller blade, the flexible coupler configured to surround the pressure adjustment body, wherein opposite ends of the flexible coupler are configured to move toward and away from each other to facilitate movement of an edge of the pressure adjustment body toward and away from the housing.

7. The method of claim 6, wherein the flexible coupler is "U" shaped and configured such that the opposite ends of the "U" move toward and away from each other to facilitate the movement of the edge of the pressure adjustment body toward and away from the housing.

8. The method of claim 6, wherein the pressure adjustment body comprises an inner portion and an outer portion and the actuator comprises one or more actuators, the method further comprising coupling the outer portion to the housing via a first flexible coupler of the flexible coupler, coupling the inner portion to the outer portion via a second flexible coupler of the flexible coupler, and displacing the inner portion and the outer portion independently with respect to each other and the housing with the one or more actuators.

9. The method of claim 6, further comprising receiving, with the centrifugal compressor, a flow of gas from a gas source; elevating, with the centrifugal compressor, a pressure of the gas to form the pressurized flow of gas; and controlling, with the centrifugal compressor, one or more gas parameters of the pressurized flow of gas in accordance with a therapy regime for delivery to a subject.

10. The method of claim 6, wherein at least a portion of the housing has a toroidal cross section.

11. A system for generating a pressurized flow of gas, the system comprising:
means for generating the pressurized flow of gas, the means for generating the pressurized flow of gas comprising at least one impeller blade;
means for housing the means for generating the pressurized flow of gas;
means for regulating pressure of the generated gas, the means for regulating pressure movably coupled to the means for housing, the means for regulating pressure comprising one or more arcuate surfaces contoured to correspond to a shape of the impeller blade;
means for displacing the means for regulating pressure with respect to the means for housing, wherein a displacement of the means for regulating pressure is configured to regulate pressure of the generated gas flow by varying a gap between the impeller blade and the one or more arcuate surfaces of the means for regulating pressure; and
means for movably coupling the means for regulating pressure to the means for housing proximate to the impeller blade, the means for movably coupling configured to surround the means for regulating pressure, wherein opposite ends of the means for movably coupling are configured to move toward and away from each other to facilitate movement of an edge of the means for regulating pressure toward and away from the means for housing.

12. The system of claim 11, wherein the means for movably coupling is "U" shaped and configured such that the opposite ends of the "U" move toward and away from each other to facilitate the movement of the edge of the means for regulating pressure toward and away from the means for housing.

13. The system of claim 11, wherein the means for regulating pressure comprises an inner portion and an outer portion and the means for displacing comprises one or more actuators, and wherein the outer portion is coupled to the housing via a first flexible coupler of the means for movably coupling, the inner portion is coupled to the outer portion via a second flexible coupler of the means for movably coupling and the one or more actuators are configured to displace the inner portion and the outer portion independently with respect to each other and the housing.

14. The system of claim 11,
wherein the means for generating the pressurized flow of gas is configured to receive a flow of gas from a gas source, elevate a pressure of the gas to form the pressurized flow of gas, and control one or more gas parameters of the pressurized flow of gas in accordance with a therapy regime for delivery to a subject; and
at least a portion of the means for housing has a toroidal cross section.

* * * * *